United States Patent [19]

Buerstinghaus et al.

[11] Patent Number: 4,859,706
[45] Date of Patent: Aug. 22, 1989

[54] PESTICIDAL COMPOSITION AND PROCESS FOR COMBATING PESTS EMPLOYING CARBOXAMIDES

[75] Inventors: Rainer Buerstinghaus, Heidelberg; Peter Hofmeister, Neustadt; Christoph Kuenast, Waldsee, all of Fed. Rep. of Germany

[73] Assignee: BASF Aktiengesellschaft, Ludwigshafen, Fed. Rep. of Germany

[21] Appl. No.: 82,326

[22] Filed: Aug. 6, 1987

[30] Foreign Application Priority Data

Aug. 19, 1986 [DE] Fed. Rep. of Germany ....... 3628082

[51] Int. Cl.[4] ................ C07C 103/19; C07C 103/58; C07C 103/34
[52] U.S. Cl. ................................ 514/624; 514/625; 514/627; 514/620; 514/630; 564/189; 564/190; 564/207; 564/221; 564/219
[58] Field of Search ............... 564/189, 190, 207, 219, 564/221; 514/624, 625, 627, 629, 630

[56] References Cited

U.S. PATENT DOCUMENTS

| | | | |
|---|---|---|---|
| 3,360,432 | 12/1967 | Newallis et al. | 514/624 |
| 4,048,327 | 9/1977 | Karrer | 424/305 |
| 4,090,865 | 5/1978 | Baker | 564/207 |
| 4,166,735 | 9/1979 | Pilgram et al. | 564/190 |
| 4,215,139 | 7/1980 | Fischer et al. | 424/300 |
| 4,329,365 | 5/1982 | Harfenist | 564/221 |
| 4,493,844 | 1/1985 | Plummer | 564/189 |

FOREIGN PATENT DOCUMENTS 0004334 10/1979 European Pat. Off. .
2633069 2/1977 Fed. Rep. of Germany .

OTHER PUBLICATIONS

Chem. Abstracts: 105: 171986s.

*Primary Examiner*—Prince E. Willis
*Assistant Examiner*—Helene Kirschner
*Attorney, Agent, or Firm*—Keil & Weinkauf

[57] ABSTRACT

Carboxamides of the general formula I

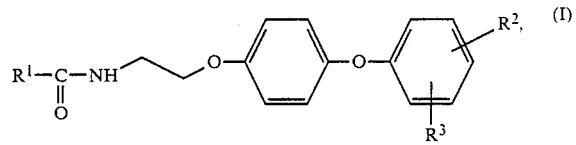

where $R^1$ is $C_1$–$C_6$-alkyl, $C_2$–$C_6$-alkenyl, $C_2$–$C_6$-alkynyl, $C_3$–$C_{10}$-cycloalkyl, $C_3$–$C_{10}$-cycloalkyenyl or $C_4$–$C_{10}$-cycloalkenylalkyl, and $R^2$ and $R^3$ are each hydrogen, halogen, $C_1$–$C_3$-alkyl, $C_1$–$C_3$-alkoxy, $C_1$–$C_3$-haloalkyl. $C_1$–$C_3$-haloalkoxy or methylthio, and their use for combating pests.

7 Claims, No Drawings

PESTICIDAL COMPOSITION AND PROCESS FOR COMBATING PESTS EMPLOYING CARBOXAMIDES

The present invention relates to novel carboxamides of the general formula I

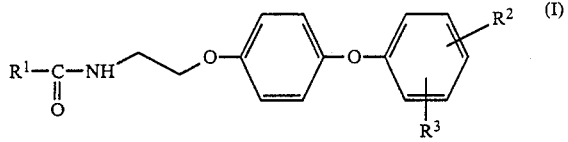

where $R^1$ is $C_1$–$C_6$-alkyl, $C_2$–$C_6$-alkenyl, $C_2$–$C_6$-alkynyl, $C_3$–$C_{10}$-cycloalkyl, $C_3$–$C_{10}$-cycloalkenyl or $C_4$–$C_{10}$-cycloalkenylalkyl and $R^2$ and $R^3$ are each hydrogen, halogen, $C_1$–$C_3$-alkyl, $C_1$–$C_3$-alkoxy, $C_1$–$C_3$-haloalkyl, $C_1$–$C_3$-haloalkoxy or methylthio.

The present invention furthermore relates to pesticides which contain the compounds I, and a process for controlling pests.

The cyclopropanecarboxylate I'

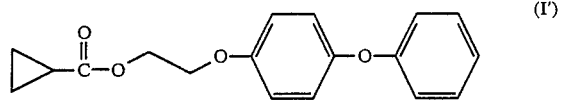

is disclosed in DE-A No. 26 33 069 and the compound I''

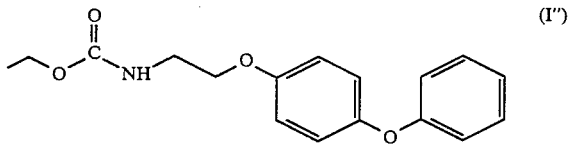

is disclosed in EP-A No. 4334, both as pesticides.

However, the action of the compounds I' and I'' is unsatisfactory.

It is an object of the present invention to provide novel carboxamides I having an improved action.

We have found that this object is achieved by the novel carboxamides I defined at the outset. We have furthermore found that the compounds I are very useful for controlling pests.

The compounds I are obtainable from 2-phenoxyethylamines II and carbonyl halides III.

The reaction of a 2-phenoxyethylamine II with a carbonyl halide III, preferably the acyl chloride of III

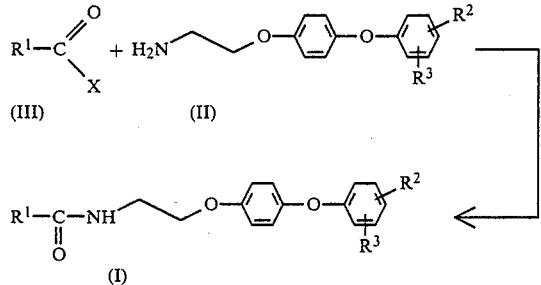

X=fluorine, chlorine, bromine or iodine in the presence of an acid acceptor at from −30° to 120° C., preferably from −10° to 80° C., particularly preferably from 0° to 50° C., and under from 1 to 10 bar gives the carboxamides I. The 2-phenoxyethylamine is a suitable acid acceptor; usually, however, the conventional basic agents are used, in particular, aliphatic, aromatic or heterocyclic amines, such as triethylamine, dimethylamine, piperidine, dimethylaniline, dimethylbenzylamine, pyridine or 4-dimethylaminopyridine. The ratio of acid acceptor to compound III is from 0.5:1 to 20:1, preferably from 0.7:1 to 5:1, particularly preferably from 0.9:1 to 1.5:1.

The starting materials II and III are usually used in a stoichiometric ratio. However, an excess of one or other component may certainly be advantageous in specific cases.

The reaction usually takes place at an adequate rate at above −30° C. In general, 100° C. need not be exceeded. Since in some cases the reaction takes place with evolution of heat, it may be advantageous to provide a means of cooling.

Some of the 2-phenoxyethylamines II are known and others can be prepared by conventional methods (EP-A1-4334). The carbonyl halides III are known and the majority are commercially available.

The reactions are advantageously carried out in a solvent or diluent. Examples of substances which are suitable for this purpose are: aliphatic and aromatic hydrocarbons and chlorohydrocarbons, such as petroleum ether, benzene, toluene, xylene, gasoline, dichloromethane, chloroform, tetrachloromethane, 1,2-dichloromethane and chlorobenzene, ethers and esters, such as diethyl and di-n-butyl ether, methyl tert.-butyl ether, tetrahydrofuran, dioxane and ethyl acetate, ketones, eg. acetone, methyl ethyl ketone and methyl isopropyl ketone, nitriles, such as acetonitrile and propionitrile, aprotic dipolar solvents, such as dimethylformamide, dimethyl sulfoxide and pyridine. Mixtures of these substances may also be used as solvents or diluents.

Some of the novel compounds of the formula I are obtained in the form of colorless or pale brown oils which can be freed from the final volatile constituents by prolonged heating under reduced pressure to moderately elevated temperatures (incipient distillation) and purified in this manner. If the compounds of the formula I are obtained in crystalline form, they may be purified by recrystallization.

The novel compounds of the formula I may furthermore be prepared by virtually any conventional method of carboxamide synthesis, for example by reacting 2-phenoxyethylamines with appropriate carboxylates, carboxylic acids or their salts, carboxylic anhydrides or ketene derivatives (cf. C. Ferri, Reaktionen der Organischen Synthese, Georg Thieme Verlag, Stuttgart 1978, page 542 and the literature cited there).

In the compounds I,
$R^1$ is straight-chain or branched $C_1$–$C_6$-alkyl, preferably $C_1$–$C_5$-alkyl, such as methyl or ethyl, particularly preferably $C_3$–$C_5$-alkyl, such as n-propyl, isopropyl, n-butyl, isobutyl, sec-butyl, tert-butyl, n-pentyl, isopentyl, 1-methylbutyl or 1,1-dimethylpropyl, straight-chain or branched $C_2$–$C_6$-alkenyl, preferably $C_2$–$C_4$-alkenyl, such as allyl, 1-methylallyl, prop-1-en-1-yl or 2-methylprop-1-en-1-yl, straight-chain or branched $C_2$–$C_6$-alkynyl, preferably $C_2$–$C_4$-alkynyl, particularly preferably ethynyl, $C_3$–$C_{10}$-cycloalkyl, preferably $C_3$–$C_6$-cycloalkyl, such as cyclobutyl, cyclopentyl or cyclohexyl, particularly preferably cyclopropyl, $C_3$–$C_{10}$-cycloalkenyl, preferably $C_3$–$C_6$-cycloalkenyl, such as cyclopent-1-en-1-yl or cyclohex-1-en-1-yl, $C_4$–$C_{10}$-cycloalkenylalkyl, preferably $C_4$–$C_8$-cycloalkenylalkyl, such as cyclopent-1-en-1-ylmethyl, 2-(cyclopent-1-en-1-yl)ethyl or cyclohex-1-en-1-ylmethyl, and $R^2$ and $R^3$ are each hydrogen, halogen, preferably fluorine, chlorine or bromine, $C_1$–$C_3$-alkyl, such as methyl, ethyl, n-propyl or isopropyl, $C_1$–$C_3$-alkoxy, such as methoxy, ethoxy, n-propoxy or isopropoxy, $C_1$–$C_3$-haloalkyl, preferably $C_1$- or $C_2$-fluoroalkyl, such as fluoromethyl, difluoromethyl, trifluoromethyl or 2,2,2-trifluoroeth-1-yl, $C_1$–$C_3$-haloalkoxy, preferably $C_1$- or $C_2$-fluoroalkoxy, such as fluoromethoxy, difluoromethoxy or trifluoromethoxy or methylthio.

Particularly preferred compounds I are those in which $R^2$ and $R^3$ are each H.

In contrast to most of the conventional active ingredients which, as contact or ingested poisons, kill, incapacitate or repel the animals, the compounds of the formula I intervene in the hormonal system of the animal organism. In the case of insects, for example, the transformation to the imago, the laying of viable eggs and the development of normal laid eggs are disturbed and the sequence of generations interrupted. The novel active ingredients are virtually completely nontoxic for vertebrates. The compounds of the formula I are moreover readily degraded to substances which occur naturally and are further decomposed by microorganisms. There is therefore no danger of accumulation. Accordingly, they can safely be used for controlling pests in animals, crops and stored goods and in water.

The carboxamides of the general formula I are suitable for effectively combating pests from the classes of insects, Arachnidae and nematodes. They may be used for protecting crops and as pesticides in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are rootknot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus lon-*

*gicaudatus, Longidorus elongatus,* and *Trichorodorus primitivus.*

The active ingredients may be applied as such, as formulations, or use forms prepared therefrom, for instance directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 2 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 2 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 2 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magensium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredient concentrations in the ready-to-use formulations may vary within a wide range. Generally, they are from 0.0001 to 10, and preferably 0.01 to 1, %. The active ingredients may also successfully be used in the ultra-low-volume method, where it is possible to apply formulations containing more than 95 wt% of active ingredient, or even the 100% active ingredient (without additives).

In the open, the amounts applied range from 0.02 to 10, and preferably 0.05 to 2.0 kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethylchrysanthemate, and alpha-cyano-3-phenoxybenzyl-alpha-isopropyl-4-chlorophenylacetate.

MANUFACTURING EXAMPLES

EXAMPLE 1

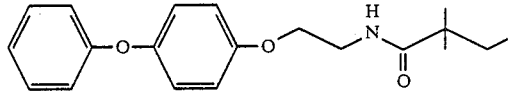

10.1 g of 2-(4-phenoxyphenoxy)-ethylamine is dissolved in 40 ml of anhydrous pyridine. While stirring, the mixture is cooled to 5° C. with the aid of an ice bath. Subsequently, a solution of 2,2-dimethylbutyryl chloride in 20 ml of methylene chloride is slowly dripped in. Upon completion of the strongly exothermic reaction the mixture is stirred for 12 hours at 25° C., poured into three times its volume of water and extracted four times with methylene chloride. The extract is washed thoroughly with water, dried over sodium sulfate and concentrated under reduced pressure. The residue is taken up in hexane/methyl tert-butyl ether (4:1) and filtered over silica gel —60 (from Merck). After the solvent has been removed a solid remains which recrystallizes from hexane/methyl tert-butyl ether to give beige-colored crystals of melting point 47°–48° C. Yield: 8.8 g (61% of theory).

$C_{20}H_{25}NO_3$ (327): calc.: C 73.4, H 7.7, N 4.3. found: C 73.3, H 7.6, N 4.2.

Infrared absorption spectra (cm$^{-1}$): 1487, 1465, 1232, 819.

EXAMPLE 2

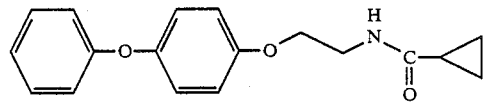

8.01 g of 2-(4-phenoxyphenoxy)-ethylamine is dissolved in 50 ml of ethyl acetate, and 5.6 g of pyridine is added to this solution. While cooling with ice, 3.65 g of cyclopropanecarboxyl chloride in 25 ml of ethyl acetate is added dropwise. When no more heat is evolved, the mixture is stirred for 10 hours at room temperature before being filtered. The clear solution is washed three times with water, three times with 5% strength hydrochloric acid, and again three times with water, dried over sodium sulfate and concentrated in a rotary evaporator. After recrystallization from ligroin/ethyl acetate (3:1), 5.4 g of an almost colorless crystalline powder is obtained having a melting range of from 101° to 102° C.
Yield: 52% of theory.
$C_{18}H_{19}NO_3$ (297).
Infrared absorption spectra (cm$^{-1}$): 1491, 1252, 1228, 1037, 841.

The compounds I listed in the tables below and which are identified by their absorption spectra were prepared in the manner given in Examples 1 and 2; other compounds corresponding to formula I may be obtained in a similar manner.

TABLE

| Ex. No. | R$^1$ | R$^2$ | R$^3$ | X | Infrared absorption (cm$^{-1}$) |
|---|---|---|---|---|---|
| 3 | n-C$_3$H$_7$ | H | H | O | 1491, 1252, 1225, 1058, 843 |
| 4 | i-C$_3$H$_7$ | H | H | O | 1490, 1250, 1227, 842 |
| 5 | CH$_2$—CH(CH$_3$)$_2$ | H | H | O | 1492, 1260, 1239, 1224, 840 |
| 6 | tert.-C$_4$H$_9$ | H | H | O | 1489, 1229, 1222, 1060 |
| 7 | —CH=CH$_2$ | H | H | O | 1491, 1252, 1229, 842 |
| 8 | —CH=CH—CH$_3$ | H | H | O | 1491, 1252, 1225, 843 |
| 9 | —CH=C(CH$_3$)$_2$ | H | H | O | 1492, 1259, 1238, 839 |
| 10 | —C(CH$_3$)=CH$_2$ | H | H | O | 1491, 1252, 1233, 1218 |
| 11 | —C≡C—H | H | H | O | |
| 15 |  | 4-Cl | H | O | |
| 16 |  | 4-F | H | O | |
| 17 |  | 3-F | H | O | |
| 18 |  | 2-F | H | O | |
| 19 |  | 2-F | 4-F | O | |
| 20 |  | 3-F | 5-F | O | |
| 21 |  | 3-Cl | 5-Cl | O | |
| 22 |  | 4-CH$_3$ | H | O | |
| 23 |  | 4-C$_2$H$_5$ | H | O | |
| 24 |  | 4-OCH$_3$ | H | O | |
| 25 |  | 4-OC$_2$H$_5$ | H | O | |
| 26 |  | 4-CH(CH$_3$)$_2$ | H | O | |
| 27 |  | 4-Br | H | O | |
| 28 |  | 4-CF$_3$ | H | O | |
| 29 |  | 4-OCF$_3$ | H | O | |

TABLE-continued

| Ex. No. | R¹ | R² | R³ | X | Infrared absorption (cm⁻¹) |
|---|---|---|---|---|---|
| 30 | $CH_3$ | H | H | O | |
| 31 | $C_2H_5$ | H | H | O | |
| 32 | cyclopentyl | H | H | O | |
| 33 | cyclohexyl | H | H | O | 1492, 1260, 1239, 1211, 839 |
| 34 | cyclobutyl | H | H | O | 1491, 1251, 1227, 842 |
| 35 | $-CH_2-$cyclopentenyl | H | H | O | |

USE EXAMPLES

In the following examples, the action of compound no. 2 according to the invention on pests was compared with that of the closest art compound:

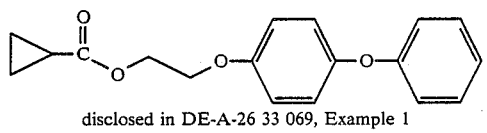

disclosed in DE-A-26 33 069, Example 1

EXAMPLE A

Breeding experiment with *Dysdercus intermedius* (cotton stainers)

200 g of sterile quartz sand to which 25 ml of aqueous active ingredient formulations had been added was filled into 1 liter jars. 20 larvae in the fourth larval stage were introduced into each jar, and fed with swollen cotton seeds.

When the animals of the control group molt into adults, the treated animals are investigated as to typical juvenoid effects such as stunted or bent wings. Such individuals are sterile and short-lived.

| Dose | % of animals with juvenoid effects | |
|---|---|---|
| (ppm) | Example 2 | Comparison |
| 10 | 100 | ca. 60 |
| 4 | 100 | ca. 60 |
| 2 | 100 | ca. 60 |
| 1 | 100 | — |
| 0.4 | 100 | — |
| 0.2 | 100 | — |
| 0.1 | 100 | — |
| 0.04 | 100 | — |
| 0.02 | ca. 60 | — |
| 0.01 | ca. 60 | — |
| Control | 0 | — |

EXAMPLE B

Breeding experiment with mosquito larvae (*Aedes aegypti*)

Active ingredient formulations were added to 200 ml of tapwater, after which 20 to 30 mosquito larvae in the fourth larval stage were introduced. The vessels were kept at 25° C. Pupation and hatching of the imagoes (after 10 to 12 days) were assessed. During the observation period a powdered food for aquarium fish was fed once.

| Dose | % of unhatched larvae | |
|---|---|---|
| (ppm) | Example 2 | Comparison |
| 0.4 | 100 | 100 |
| 0.2 | 100 | 100 |
| 0.1 | 100 | <50 |
| 0.04 | 100 | 100 |
| 0.02 | 100 | 0 |
| 0.01 | 100 | 0 |
| 0.004 | <50 | 0 |
| 0.002 | 100 | 0 |
| 0.001 | 0 | 0 |
| 0.0004 | 0 | 0 |
| Control | 0 | 0 |

EXAMPLE C

Growth inhibition in *Prodenia litura* (in a treated medium)

100 g of the standard nutrient medium for Prodenia was filled into 250 ml beakers and carefully mixed with aqueous formulations of the active ingredients. After the vessels had cooled, 5 caterpillars of the third larval stage were introduced into each vessel and the vessels stored at 23° C. The animals were later assessed for typical juvenoid effects such as a red coloring of the caterpillars, destroyed pupation burrow, and non-pupation.

| Dose | % of animals with juvenoid effects | |
| --- | --- | --- |
| (ppm) | Example 2 | Comparison |
| 1.0 | 100 | 0 |
| 0.4 | 100 | 0 |
| 0.2 | ca. 60 | 0 |
| 0.1 | ca. 60 | 0 |
| 0.04 | 0 | 0 |
| 0.02 | 0 | 0 |
| 0.01 | 0 | 0 |
| Control | 0 | 0 |

We claim:

1. A pesticidal composition which comprises: a carrier or diluent and an effective amount of a carboxamide of the formula I

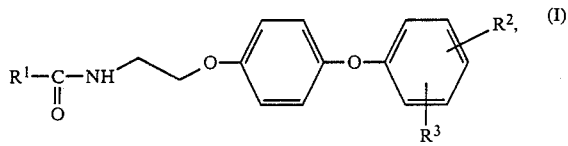

where $R^1$ is $C_1$–$C_6$-alkyl, $C_2$–$C_6$-alkenyl, $C_2$–$C_6$-alkynyl, $C_3$–$C_{10}$-cycloalkyl, $C_3$–$C_{10}$-cycloalkenyl or $C_4$–$C_{10}$-cycloalkenylalkyl, and $R^2$ and $R^3$ are each hydrogen, halogen, $C_1$–$C_3$-alkyl, $C_1$–$C_3$-alkoxy, $C_1$–$C_3$-haloalkyl, $C_1$–$C_3$-haloalkoxy or methylthio.

2. A composition as set forth in claim 1, containing from 0.1 to 9.5 wt% of a carboxamide of the formula I.

3. A composition as described in claim 1, wherein $R^1$ is isopropyl.

4. A composition as set forth in claim 1, wherein $R^1$ of the active ingredient is cyclopropyl and $R^2$ and $R^3$ are each hydrogen.

5. A process for combating pests, wherein the pests or the areas to be kept free from pests are treated with an effective amount of a carboxamide of the formula I

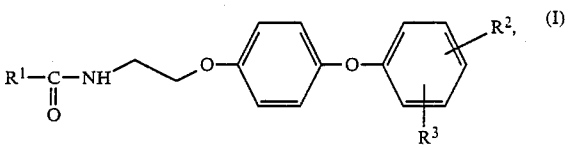

where $R^1$ is $C_1$–$C_6$-alkyl, $C_2$–$C_6$-alkenyl, $C_2$–$C_6$-alkynyl, $C_3$–$C_{10}$-cycloalkyl, $C_3$–$C_{10}$-cycloalkenyl or $C_4$–$C_{10}$-cycloalkenylalkyl, and $R^2$ and $R^3$ are each hydrogen, halogen, $C_1$–$C_3$-alkyl, $C_1$–$C_3$-alkoxy, $C_1$–$C_3$-haloalkyl, $C_1$–$C_3$-haloalkoxy or methylthio.

6. A process as defined in claim 5, wherein $R^1$ is isopropyl.

7. A process for combating pests as defined in claim 5, wherein $R^1$ of the active ingredient is cyclopropyl and $R^2$ and $R^3$ are each hydrogen.

* * * * *